United States Patent
Marliere et al.

(10) Patent No.: US 7,736,899 B1
(45) Date of Patent: Jun. 15, 2010

(54) CELLS AND METHOD FOR PRODUCING PROTEINS COMPRISING AN UNCONVENTIONAL AMINO ACID

(75) Inventors: Philippe Marliere, Etiolles (FR); Volker Doring, Paris (FR); Henning Mootz, Marburg (DE)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/830,669

(22) PCT Filed: Oct. 28, 1999

(86) PCT No.: PCT/FR99/02628

§ 371 (c)(1),
(2), (4) Date: Apr. 30, 2001

(87) PCT Pub. No.: WO00/24922

PCT Pub. Date: May 4, 2000

(30) Foreign Application Priority Data

Oct. 28, 1998 (FR) .................................. 98 13533

(51) Int. Cl.
*C12N 15/00* (2006.01)
*C12N 1/20* (2006.01)
*C12P 21/00* (2006.01)

(52) U.S. Cl. .................... 435/471; 435/440; 435/252.8; 435/71.2

(58) Field of Classification Search .................... 435/6, 435/29, 320.1, 252.3, 455, 471, 252, 33, 435/243; 536/23.1
See application file for complete search history.

(56) References Cited

OTHER PUBLICATIONS

Murgola et al. Suppressors of a UGG missense mutation in *Escherichia coli*. J Bacteriol. vol. 143, No. 1, pp. 285-292, Jul. 1980.*
Seale et al. Amino acid replacements resulting from suppression and missense reversion of a chain-terminator mutation in Neurospora. Genetics. vol. 86, No. 2 Pt. 1, pp. 261-274, Jun. 1977.*
Chiu et al. Genetic and molecular analysis of a tRNA(Leu) missense suppressor of nudC3, a mutation that blocks nuclear migration in *Aspergillus nidulans*. Genetics. vol. 145, No. 3, pp. 707-714, Mar. 1997.*
Drabkin et al. Initiator-elongator discrimination in vertebrate tRNAs for protein synthesis. Mol Cell Biol. vol. 18, No. 3, pp. 1459-1466, Mar. 1998.*
Landes et al. A structure-based multiple sequence alignment of all class I aminoacyl-tRNA synthetases. Biochimie vol. 77, pp. 194-203, 1995.*
B. Lemeignan, et al., "Phenotypic suppression by incorporation of an alien amino acid", Journal of Molecular Biology, vol. 231, No. 2, May 1993, pp. 161-166.
V. Döring, et al., "Reassigning Cysteine in the genetic code of *Escherichia coli*", Genetics, vol. 150, No. 2, Oct. 1998, pp. 543-551.
J. D. Bain, et al., "Ribosome-mediated incorporation of a non-standard amino acid into a peptide through expansion of the genetic code", Nature, vol. 356, Apr. 9, 1992, pp. 537-539.
M. Ibba, "Strategies for in vitro and in vivo translation with non-natural amino-acids", Biotechnology and Genetic Engineering Reviews, vol. 13, 1996, pp. 197-216.

* cited by examiner

*Primary Examiner*—Jennifer Dunston
(74) *Attorney, Agent, or Firm*—Oblon, Spivak, McClelland, Maier & Neustadt, L.L.P.

(57) ABSTRACT

The present invention relates to a method for providing bacterial or yeast cells with the capacity to produce a protein, the amino acid sequence of which comprises at least one unconventional amino acid. The method involves (a) introducing at least one missense mutation in a target codon of a gene encoding a protein required for the growth of the bacterial or yeast cells, where the mutated protein synthesized from the mutated gene is not functional in the bacterial or yeast cells. The method also involves (b) selecting the bacterial or yeast cells obtained in (a) in a culture medium which (1) does not contain a nutrient compensating for the loss of functionality of the mutated protein and (2) contains an unconventional amino acid which restores the functionality of the protein required for growth of the bacterial or yeast cells, in which the unconventional amino acid is that encoded by the target codon. The method also involves culturing the bacterial or yeast cells obtained in (b) in a culture medium containing the amino acid encoded by the target codon.

42 Claims, No Drawings

SEQUENCE LISTING

```
<160> NUMBER OF SEQ ID NOS: 8

<210> SEQ ID NO 1
<211> LENGTH: 49
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
tggataaaat ggcgctggca ccggtacatg cattcttcca gttctatgt            49

<210> SEQ ID NO 2
<211> LENGTH: 18
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
ggtgtgatca tgatggtc                                              18

<210> SEQ ID NO 3
<211> LENGTH: 18
```

```
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
cctgcaagat ggattccc                                              18

<210> SEQ ID NO 4
<211> LENGTH: 19
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
cgcgccgcat tattgtttc                                             19

<210> SEQ ID NO 5
<211> LENGTH: 19
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
gtctggaccg gtggcgaca                                             19

<210> SEQ ID NO 6
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
gggaattcgg tgtgtgaaat tgccgcagaa cg                              32

<210> SEQ ID NO 7
<211> LENGTH: 33
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
ggcaagcttc cagtatttca cggggagtta tgc                             33

<210> SEQ ID NO 8
<211> LENGTH: 49
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
tggataaaat ggcgctggca ccgatacatg cattcttcca gttctatgt            49
```

CELLS AND METHOD FOR PRODUCING PROTEINS COMPRISING AN UNCONVENTIONAL AMINO ACID

This application is a national stage entry under 35 U.S.C. §371 of PCT international application number PCT/FR99/02628, filed Oct. 28, 1999.

The present invention relates to methods which allow prokaryotic or eukaryotic cells to acquire the capacity to produce proteins the amino acid sequences of which comprise at least one unconventional amino acid, to methods for selecting said cells, to methods for producing and for purifying said proteins, and also to the cells and proteins obtained using the methods and processes according to the invention. The invention also comprises the uses of said cells and proteins in various domains, such as the therapeutic, cosmetic or diagnostic domain or the domain of biosynthesis, or the biodegradation of organic compounds.

An increasing number of proteins which are mass-produced using recombinant organisms are employed as catalysts in the chemical industry or as therapeutic agents. The search for novel proteins with diversified functions is the subject of intense activity, either by screening the proteins of extremophilic organisms, or by creating protein variants by mutagenesis and screening. However, the chemical variability of the proteins which can be produced in living organisms remains limited by the invariance of the genetic code, i.e. restricted to combinations of a canonical set of 20 amino acids. If descendence of natural species could be progressively remodeled in the laboratory so as to adopt various genetic codes, protein evolution could be redirected and artificial sources of biodiversity thereby established.

Experimental deviation of the genetic code is the only path which would make it possible to overcome this limitation. An alternative genetic code might specify a smaller or larger set of amino acids, a set substituted with noncanonical monomers or a set of canonical amino acids among which the codons are redistributed. The specification of additional amino acids in living lines would lend itself to many uses, the most generic of which would be the establishment of artificial biodiversity.

The permanent or transient incorporation of a single additional amino acid, carrying a chemical motif which could react without modifying the conventional amino acids, would be sufficient to establish novel protein functionalization methods. This is precisely the subject of the present invention.

A subject of the invention is a method which allows cells to acquire the capacity to produce a protein the amino acid sequence of which comprises at least one unconventional amino acid, characterized in that it comprises the following steps:
a) transforming said cells by at least one introduction of a missense mutation in a target codon of a gene encoding a protein required for the growth of said cells, said protein synthesized from the gene thus mutated no longer being functional;
b) where appropriate, culturing the cells obtained in step a) in a culture medium containing the nutrient required by the loss of functionality of said protein thus mutated; and
c) culturing the cells obtained in step a) or b) in a culture medium containing the amino acid encoded by said target codon.

In the present description, the term "protein" will be intended to also refer to peptides or poly-peptides, and also to the corresponding glycoproteins when said proteins are glycosylated.

In the present description, the term "unconventional amino acid" will be intended to also refer to any amino acid other than the amino acids incorporated by ribosomes during the biosynthesis of proteins synthesized by prokaryotic or eukaryotic, unicellular or multicellular organisms, and also to any amino acid incorporated in place of the amino acid which should normally be incorporated at this site with regard to the translated nucleic acid sequence.

In the present description, the term "missense mutation" will be intended to also refer to a mutation which transforms a codon which represents an amino acid into a codon which encodes another amino acid, the latter, where appropriate, being unable to replace the amino acid of origin so as to give a functional protein, in the protein at the site of the amino acid residue of origin.

In the present description, the expression "protein required for the growth of cells" will be intended to also refer to a protein which, when it is synthesized by cells in a functional manner, allows said cells to grow under given culture conditions and which, when it is synthesized by cells in a nonfunctional manner, requires the introduction of an additional nutrient into said given culture medium in order to allow said cells to grow. Such nonfunctional proteins can, for example, be synthesized by cells subsequent to conditional mutations such as a photosensitive-type mutation.

In order to illustrate with an example, but without being limited thereto, mention may be made in particular of the thymidylate synthase protein of *E. coli*, which has a catalytic site occupied by cysteine at position 146 of its amino acid sequence, and the corresponding mutations of the gene (thyA) of which cause a nutritional requirement for thymine or thymidine, no other amino acid being able to replace cysteine at this site.

In the present description, the term "target codon" will be intended to refer to the three-nulceotide-base codon transformed by the missense mutation.

The invention also comprises a method according to the invention, characterized in that the culture medium of step c) does not contain the nutrient required by the loss of functionality of said mutated protein.

According to the invention, step c) for culturing said cells can comprise a series of cultures of said cells in a culture medium containing the amino acid encoded by said target codon, each of said cultures of the series being prepared as far as obtaining the stationary growth phase and followed by washing of the cells obtained, the number of cultures of the series being sufficient to allow the selection of mutations which increase the suppression of said missense mutation of said mutated gene, and the propagation of the allele corresponding to said mutated gene.

The invention also relates to a method according to the invention, characterized in that the missense mutation is chosen from missense mutations which spontaneously reverse only at very low frequency, of the order of one organism from at least $10^{15}$.

Preferably, the missense mutation will be chosen from missense mutations which transform a target codon of a gene encoding a protein required for the growth of said cell, into a codon which, in comparison with the target codon, exhibits a change of at least two bases, more preferably three bases.

Preference is also given to the methods according to the invention, characterized in that the target codon encodes an amino acid which has a small steric volume and/or which is amphiphilic and/or which has a steric volume smaller than or substantially equal to the steric volume of the amino acid encoded by the missense mutation.

Among the target codons, preference is in particular given to target codons encoding cysteine and missense mutations chosen from missense mutations which transform a target codon into a codon encoding valine or isoleucine.

The invention also relates to a method according to the invention, characterized in that step a) for transforming said cells is carried out using a vector comprising a sequence of said gene encoding a protein required for the growth of said cells, including said missense mutation, in particular using a plasmid vector.

Such vectors will be prepared according to methods commonly used by those skilled in the art, and the clones resulting therefrom can be introduced into said cells by usual methods of genetic recombination, such as for example lipofection, electroporation or heat-shock.

In another aspect, a subject of the invention is a method for selecting cells capable of producing a protein the amino acid sequence of which comprises at least one unconventional amino acid, characterized in that it comprises steps a), where appropriate b), and c) of a method according to the invention, and selecting the cells capable of growing in step c).

Preferably, the method for selecting cells according to the invention will also comprise a step d) for culturing the cells in step c) in a culture medium containing said amino acid encoded by said target codon, the concentration of said amino acid possibly being at a concentration higher than the concentration of said amino acid used in step c), and choosing the cells sensitive to the concentration of said amino acid used in step d).

The expression "cell sensitive to a chemical or biochemical compound or to a given concentration of said compound" is intended to refer to a cell the growth of which is partially or totally inhibited when it is cultured in a culture medium containing said chemical or biochemical compound or said concentration of said compound.

The invention also comprises a method for selecting cells according to the invention, characterized in that the aminoacyl-tRNA synthetase which recognizes the amino acid encoded by said missense mutation of said selected cells is capable of charging onto one of its associated tRNAs an unconventional amino acid or an amino acid other than said amino acid encoded by said missense mutation.

In the present description, the term "associated tRNA" is intended to refer to a tRNA which is recognized by the aminoacyl-tRNA synthetase which recognizes an amino acid, and which can transfer said amino acid.

The invention also comprises a method for selecting mutant cells according to the invention, characterized in that the nucleic acid sequence of the gene encoding said aminoacyl-tRNA synthetase includes at least one mutation compared with the sequence of the corresponding wild-type gene, said mutation not having been introduced by a technique of genetic recombination.

According to another aspect, a subject of the invention is the prokaryotic or eukaryotic cells obtained using a method according to the invention.

Among the cells which can be used for these purposes, mention may of course be made of bacterial cells, such as *E. coli*, but also yeast cells, as well as animal cells, in particular mammalian cell cultures, such as in particular Chinese hamster ovary (CHO) cells, and also insect cells.

The invention also relates to the isolated prokaryotic or eukaryotic cells capable of producing a protein the amino acid sequence of which comprises at least one unconventional amino acid, characterized in that they comprise an aminoacyl-tRNA synthetase which recognizes a given amino acid and which is capable of charging onto one of its associated tRNAs an unconventional amino acid or an amino acid other than said given amino acid, and in that the nucleic acid sequence of the gene encoding said aminoacyl-tRNA synthetase includes at least one mutation compared with the sequence of the corresponding wild-type gene, said mutation not having been introduced by a technique of genetic recombination.

Thus, the invention relates to a method for selecting cells, based on the constitution, by the cell, of a metabolic pathway required for its growth, making it possible to obtain cells capable of producing a noncanonical acyl-tRNA capable of charging an unconventional amino acid.

Among the cells according to the invention, preference is given to bacterial cells characterized in that they are chosen from the following cells deposited at the CNCM (Collection Nationale de Culture de Microorganismes [National Collection of Microorganism Cultures], Institut Pasteur 28, rue du Dr Roux 75724 Paris Cédex 15, France):
a) *E. coli* strain deposited at the CNCM under the No. I-2025 on May 25, 1998,
b) *E. coli* strain deposited at the CNCM under the No. I-2026 on May 25, 1998,
c) *E. coli* strain deposited at the CNCM under the No. I-2027 on May 25, 1998,
d) *E. coli* strain deposited at the CNCM under the No. I-2339 on Oct. 26, 1999,
e) *E. coli* strain deposited at the CNCM under the No. I-2340 on Oct. 26, 1999, and
f) *E. coli* strain deposited at the CNCM under the No. I-2341 on Oct. 26, 1999.

The *E. coli* strain K12, deposited at the CNCM under the No. I-2025 and identified under the reference β5366, is a descendent of the strain MG1655 (wt *E. coli* K12), which includes the following characteristics:
  deletion at the thyA locus and replacement with an erythromycin resistance gene,
  carries a plasmid pTZ18 (col E1 replicon, bla$^+$) with the Cys146GUA allele of thymidylate synthase.

The *E. coli* strain K12, deposited at the CNCM under the No. I-2026 and identified under the reference β8144, is a descendant of the strain MG1655 (wt *E. coli* K12), which includes the following characteristics:
  deletion at the thyA locus and replacement with an erythromycin resistance gene, carries a plasmid pTZ18 (col E1 replicon, bla$^+$) with the Cys146GUA allele of thymidylate synthase.

The *E. coli* strain K12, deposited at the CNCM under the No. I-2027 and identified under the reference β8146, is a descendant of the strain MG16555WT *E. coli* K12), which includes the following characteristics:
  deletion at the thyA locus and replacement with an erythromycin resistance gene,
  carries a plasmid pTZ18 (col E1 replicon, bla$^+$) with the Cys146GUA allele of thymidylate synthase.

The *E. coli* strain K12, deposited at the CNCM under the No. I-2339 and identified under the reference β5479, is a descendant of the strain MG1655 (wt *E. coli* K12), which includes the following characteristics:
  deletion at the thyA locus and replacement with an erythromycin resistance gene,
  deletion at the nrdD locus and replacement with a kanamycin resistance gene,
  carries the R223H allele of the valS gene,
  carries a plasmid pTZ18 (col E1 replicon, bla$^+$) with the Cys146GUA allele of thymidylate synthase.

The *E. coli* strain K12, deposited at the CNCM under the No. I-2340 and identified under the reference β5485, is a descendant of the strain MG1655 (wt *E. coli* K12), which includes the following characteristics:
  deletion at the thyA locus and replacement with an erythromycin resistance gene,
  deletion at the nrdD locus and replacement with a kanamycin resistance gene,
  carries the Val 276 Ala chromosomal allele of the valS gene,
  carries a plasmid pTZ18 (col E1 replicon, bla+) with the Cys146GUA allele of thymidylate synthase.

The *E. coli* strain K12, deposited at the CNCM under the No. I-2341 and identified under the reference β5486, is a descendant of the strain MG1655 (wt *E. coli* K12), which includes the following characteristics:
  deletion at the thyA locus and replacement with an erythromycin resistance gene,
  deletion at the nrdD locus and replacement with a kanamycin resistance gene,
  carries the Asp 230 Asn chromosomal allele of the valS gene,
  carries a plasmid pTZ18 (col E1 replicon, bla+) with the Cys146GUA allele of thymidylate synthase.

The invention also comprises the use of a method or of a cell according to the invention for producing protein, in particular recombinant protein, the amino acid sequence of which comprises at least one unconventional amino acid.

In another aspect, the invention relates to a process for producing a protein the amino acid sequence of which comprises at least one unconventional amino acid, characterized in that it comprises the following steps:
a) where appropriate, selecting a cell by a method according to the invention;
b) culturing said cell selected in step a) or a cell according to the invention in a culture medium and under culture conditions which allow the growth of said cell; and
c) isolating said protein comprising at least one unconventional amino acid from the culture supernatant and/or from the cell pellet obtained in step b).

Among the proteins which can be produced by a process according to the invention, mention may be made, but without being limited thereto, of proteins which, through the incorporation of at least one unconventional amino acid, make it possible to obtain a desired activity which a protein the sequence of which includes only conventional amino acids does not make it possible to obtain. The term "activity" is intended to refer, in general, to any activity such as a physiological or biological activity, even partial, relating to unicellular or multicellular organisms, such as for example a structural or biochemical activity, for example an enzymatic or antigenic activity, an activity of antibody type, or an activity which modulates, regulates or inhibits biological activity, or such that it allows the implementation thereof in a process for biosynthesizing or for biodegrading chemical or biochemical compounds.

Among the proteins which can be produced by a process according to the invention, mention may also be made of proteins for which the incorporation of at least one unconventional amino acid is carried out such that there results therefrom no substantial modification of the biological activity of the corresponding unmodified protein. Besides the conserved biological activity of the corresponding unmodified protein, these proteins according to the invention will have an unconventional amino acid with specific properties which may be advantageously exploited.

Among the specific properties conferred by the presence of an unconventional amino acid, mention may be made in particular of the properties linked to the presence of a functional group on said unconventional amino acid, capable of reacting easily and specifically with a chemical or biochemical compound under conditions which make it possible not to modify the activity of the protein or which avoid modifying the conventional amino acids.

The presence of this specific functional group may advantageously be used, for example, for:

(i) purifying any protein, in particular any recombinant protein, which incorporates said unconventional amino acid;

(ii) coupling such a protein to a solid support;

(iii) coupling to such a protein molecules capable of being detected, such as spectroscopic probes of varied nature;

(iv) coupling to such a protein lipophilic or hydro-philic polymers which allow the solubilization thereof in solvents or which allow masking against recognition by antibodies;

(v) coupling such a protein to a polynucleotide;

(vi) coupling such a protein to a chemical or biochemical compound the presence of which makes it possible to increase, to decrease, to modify, to regulate or to target the biological activity of said protein, or to modify the bioavailability thereof as a compound for therapeutic use; or (vii) permanently attaching to such a protein a coenzyme which otherwise would diffuse in solution.

According to the present invention, the incorporation of at least one unconventional amino acid may relate to amino acids responsible for specificity or for the activity, or responsible for the structural conformation, for the charge, for the hydrophobicity or for the multimerization capacity of the corresponding unmodified protein. Thus, proteins of equivalent, increased or decreased activity, or of specificity which is equivalent, more restricted or broader than the corresponding unmodified protein containing conventional amino acids may be created.

The term "unmodified protein" is intended to refer to the wild-type or recombinant protein which consists of conventional amino acids, and from which is derived the protein comprising the unconventional amino acid.

Preferably, the production process according to the invention is characterized in that said culture medium of step b) which allows the growth of said cell contains said unconventional amino acid or a precursor thereof.

According to one particular embodiment, a production process according to the invention is characterized in that said unconventional amino acid is synthesized by said cell, the synthesis of said unconventional amino acid possibly being increased by genetic modification of said cell.

The invention also relates to a process for producing a protein the amino acid sequence of which comprises at least one unconventional amino acid according to the invention, characterized in that said cell is auxotrophic for the amino acid encoded by said target codon.

Also included in the present invention are the processes according to the invention, characterized in that said cell comprises a homologous or heterologous gene of interest the coding sequence of which includes at least one target codon.

In general, the gene of interest will encode a messenger RNA which will then be translated into a protein of interest.

The gene of interest can be isolated by any conventional technique, such as cloning or PCR (Polymerase Chain Reaction), or chemically synthesized. It can be of genomic (possessing one or more introns) or complementary DNA (cDNA) type. The protein of interest can consist of a mature protein, a precursor, and in particular a precursor intended to be secreted and comprising a signal peptide, a truncated protein, a chimeric protein originating from the fusion of sequences of diverse origins, or a mutated protein having improved and/or modified biological properties.

In general, the homologous or heterologous gene of interest may be chosen from genes encoding any protein which can be used as a therapeutic or cosmetic compound, or as a diagnostic reagent or as a compound which can be used in a biosynthesis or biodegradation process.

By way of examples, mention may be made of genes of interest encoding the following proteins of interest:

cytokines or lymphokines (α-, β- and γ-interferons, interleukins, and in particular IL-2, IL-6, IL-10 or IL-12, tumor necrosis factors (TNFs), colony stimulating factors (GM-CSF, C-CSF, M-CSF, etc.));

cell or nuclear receptors, in particular those recognized by pathogenic organisms (viruses, bacteria or parasites), or the ligands thereof;

proteins involved in a genetic disease (factor VII, factor VIII, factor IX, dystrophin or minidystrophin, insulin, CFTR (Cystic Fibrosis Transmembrane Conductance Regulator) protein, growth hormones (hGH));

enzymes (urease, renin, thrombin, etc.) or any enzymes involved in the metabolism or biosynthesis of proteins, of lipids, of nucleic acids, of sugars, of amino acids, of fatty acids or of nucleotides;

enzyme inhibitors (α-1-antitrypsin, antithrombin III, viral protease inhibitors, etc.);

compounds with an antitumor effect, capable of inhibiting at least partially the initiation or progression of tumors or cancers (antibodies, inhibitors acting on cell division or on transduction signals, tumors suppressor gene expression products, for example p53 or Rb, proteins which stimulate the immune system, etc.);

class I or II major histocompatibility complex proteins, or regulatory proteins which act on the expression of the corresponding genes proteins capable of inhibiting a viral, bacterial or parasitic infection or the development thereof (antigenic proteins having immunogenic properties, antigenic epitopes, antibodies, etc.);

toxins such as ricin, cholera, diphtheria, etc. toxins, or immunotoxins;

markers (β-galacatosidase, peroxidase, etc.); and luciferase, GFP (green fluorescent protein), etc.

The invention also comprises a process for producing a protein according to the invention, characterized in that the culture medium of step b) also comprises the compounds required for inducing the synthesis of the protein encoded by said gene of interest. These compounds are known to those skilled in the art and depend, in particular, on the cell and on the homologous or heterologous gene selected.

The invention also relates to a process according to the invention, characterized in that the biological activity of the protein encoded by said gene of interest is at least partially conserved after the incorporation of said unconventional amino acid at the level of the target codon of said gene of interest.

The invention also relates to a process according to the invention, characterized in that the unconventional amino acid is chosen from unconventional amino acids of formula I and of configuration L

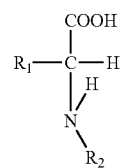

in which:

$R_1$ or $R_2$ represents radicals containing a functional group capable of reacting selectively, preferably chosen from aldehyde, ketone, ethenyl, ethynyl and nitrile groups.

Among these groups, preference is given particularly to the oxo(aldehyde or ketone) group with selective reactivity which would facilitate the chemical functionalization of the proteins. Other simple groups, such as the ethynyl group, would also lend themselves to selective reactions. A vast collection of experiments conducted with the aid of systems of a cellular (ex vivo) translation and of acyl-tRNAs synthesized in vitro has demonstrated that a large variety of acyl groups can be transferred on the ribosome in response to a codon read by the tRNA. Briefly, lateral modifications of amino acids all appear to be compatible with translation (to date, no amino acid having a side chain which would be bulky enough to block translation has been found); substitutions of the amino motif to an alkylamino, to a hydroxyl and to a hydrazino motif are compatible with ribosome-catalyzed transpeptidation chemistry (Bain et al. 1991) (it is known that the ribosome can form polyesters in addition to conventional polyamides); the substitution of the alpha hydrogen of the $H_2NCH(R)$—COOH motif with an alkyl(methyl) group, or the inversion of configuration at the alpha carbon (D-amino acids) is not, on the other hand, accepted by the ribosome.

A subject of the invention is also a process according to the invention, for protein functionalization.

The invention also relates to a protein purification process, characterized in that it comprises the following steps:

a) incorporating into the amino acid sequence of said protein an unconventional amino acid containing a functional group capable of reacting selectively, using a process according to the invention;

b) bringing the solution containing the protein obtained in step a) into contact with a support comprising a compound capable of reacting specifically with said functional group and of attaching specifically said protein; and c) isolating said protein attached to the support.

The processes for purifying protein, which may be natural or recombinant, conventionally used by those skilled in the art generally employ methods used individually or in combination, such as fractionation, chromatography methods, immunoaffinity techniques using specific mono- or polyclonal antibodies, etc. These methods are sometimes long and tedious and do not always make it possible to obtain the specific activity, the level and the yield of purification desired. The presence of a specific functional group on the protein to be purified, which group is capable of reacting selectively with the purification support without modifying the activity of the protein, would greatly facilitate the purification of protein required for the use thereof.

The invention also relates to a process for attaching a protein to a chemical or biochemical compound, characterized in that it comprises the following steps:

a) incorporating into the amino acid sequence of said protein, by a process according to the invention, an unconventional amino acid containing a functional group capable of reacting selectively;

b) bringing the protein obtained in step a) into contact with said chemical or biochemical compound comprising a group capable of reacting specifically with said functional group in a medium allowing the reaction.

Preferably, the attachment of a protein to a chemical or biochemical compound is an attachment by covalent bonding.

The chemical or biochemical compounds which can be used in said attachment process according to the invention may be chosen from all compounds capable of reacting with the functional group of the incorporated unconventional amino acid.

In the present description, the term "protein complex" is intended to refer to the product obtained in step b) of the process described above, comprising a protein according to the invention attached to a chemical or biochemical compound.

The invention also comprises a process according to the invention, characterized in that said chemical or biochemical compound is, itself, attached to a solid support or is a constituent compound of a solid support.

The invention also relates to a process according to the invention, for preparing a protein complex.

Preferably, the invention comprises the processes of the invention, characterized in that said attached protein or said chemical or biochemical compound is chosen from therapeutic, cosmetic or diagnostic compounds.

Said attached protein will be chosen, in particular, from proteins the amino acid sequence of which comprises an unconventional amino acid according to a process of the invention, and for which the corresponding wild-type or recombinant unmodified protein is chosen from proteins which can be used as therapeutic or cosmetic compounds or as diagnostic reagents.

Preferably, the processes according to the invention are characterized in that the chemical or biochemical compound is chosen from compounds capable of modifying the biological activity of the attached protein.

The expression "compounds capable of modifying the biological activity of another compound" is intended to refer to a compound capable of increasing, of decreasing or of regulating the biological activity of said other compound.

The invention also comprises a process according to the invention, characterized in that the chemical or biochemical compound is chosen from compounds the biological activity of which can be modified by the attached protein.

The invention also comprises a process according to the invention, characterized in that the chemical or biochemical compound is chosen from compounds comprising a protein, a polynucleotide, a fatty acid, a sugar or a natural or synthetic polymer.

According to another aspect, a subject of the invention is the proteins, in particular the recombinant proteins, and the protein complexes obtained by a process according to the invention.

The invention also comprises a method for selecting compounds capable of binding to a protein according to the invention or capable of binding to the chemical or biochemical compound of the protein complex according to the invention. Among these methods, mention may be made, as an example, of a method characterized in that it comprises the following steps:

a) bringing said compound which may be selected into contact with the protein or the protein complex according to the invention, said protein or protein complex possibly being in particular attached to a solid support;

b) determining the capacity of said compound to bind with the protein or the protein complex according to the invention.

The compounds which may be selected can be organic compounds, such as proteins or carbohydrates, or any other already known organic or inorganic compounds, or novel organic compounds developed using molecular modeling techniques and obtained by chemical or biochemical synthesis, these techniques being known to those skilled in the art.

The cells according to the invention may also advantageously serve as a model, and be used in processes for studying, identifying and/or selecting proteins according to the invention or compounds which may possess a desired activity.

The invention also relates to the use of a protein or of a protein complex according to the invention as a diagnostic reagent, and also to the diagnostic processes, in particular for specifically detecting, identifying, locating and/or assaying polypeptides or polynucleotides, using a protein or a protein complex according to the invention.

Proteins having incorporated at least one unconventional amino acid and having partially or totally conserved the initial activity of the corresponding unmodified wild-type or recombinant proteins, such as antibodies, antigens, enzymes or the biologically active fragments thereof known to be used in diagnostic processes are, specifically, included in the proteins according to the invention.

Similarly, protein complexes formed from a protein according to the invention and a chemical or biochemical compound, such as complexes comprising an antibody, an antigen or an oligonucleotide probe coupled to an enzyme, to a substrate or to a molecule capable of being detected, are included in the protein complexes according to the invention.

Among the diagnostic processes according to the invention, mention may be made, for example, of the processes comprising the following steps:

a) bringing the biological sample which may contain the compound sought into contact with a protein or a protein complex according to the invention, said protein or protein complex possibly being in particular attached to a solid support; and b) revealing, identifying, locating and/or assaying the complex formed between the compound sought and a protein or a protein complex according to the invention.

Those skilled in the art will be able to adapt the known standard diagnostic processes to the proteins or the protein complexes according to the invention.

The specific techniques and reagents which allow the complex formed to be revealed, identified, located and/or assayed, and which may be used in the processes of the invention, are also well known to those skilled in the art and are, for example, the ELISA, RIA, immunofluorescence or PCR techniques, or other techniques for amplifying a target nucleic acid which are known to those skilled in the art.

The invention also relates to a diagnostic kit or pack, in particular for specifically detecting, identifying, locating and/or assaying proteins or polynucleotides, characterized in that it contains a protein or a protein complex according to the invention.

The invention also relates to the use of a protein, of a protein complex or of a cell according to the invention, for preparing a pharmaceutical or cosmetic composition.

Finally, a subject of the invention is a pharmaceutical or cosmetic composition comprising a protein, a protein complex or a cell according to the invention.

Other characteristics and advantages of the invention appear in the remainder of the description with the examples hereinafter.

EXAMPLES

Example 1

Construction of an *E. coli* strain including a Cys→Val missense mutation at the thymidylate synthase active site and creating a nutritional requirement for thymine, thymidine or cysteine.

The artificial alleles of the thyA gene are constructed by site-directed mutagenesis of the plasmid pTS0 (Lemeignan et al. 1993), which derives from the plasmid pTZ18R (BioRad) by insertion of the wild-type thyA gene of *E. coli*. The site-directed mutagenesis using an oligonucleotide is carried out according to the method described by Kunkel et al. (1987) on the phagemid pTS0. The preparation of the single-stranded matrix of pTS0, amplified in the strain RZ1032 (Kunkel et al., 1987) (Hfr KL16 P045 [lysA(61-62)] dut1 ung1 thi1 relA1 supE44 zbd-279::Tn10) is carried out according to the protocol described by Sambrook et al. (1989). A 5'-phosphorylated oligonucleotide (purchased from the company Genome Express) is used as a mutagenic primer:

Oligodeoxynucleotide 1 (SEQ ID NO:1): 5' pTG-GATAAAATGGCGCTGGCACCGGTACATG-CATTCTTCCAGTTCTATGT The hybridization of this oligonucleotide with the single-stranded matrix in each of the two constructions is carried out with 10 ng of oligonucleotide and 0.2 µl of matrix in a volume of 10 µl of a buffer solution containing 20 mM of Tris-HCl, pH 7.5, 2 mM of EDTA and 50 mM of sodium chloride. The tubes are incubated for 5 min at 70° C., and then gradually cooled to 30° C. 0.5 mM of each of the dNTPs, 1 mM of ATP, 10 mM of Tris-HCl at pH 7.5, 10 mM of magnesium chloride, 2 mM of dithiothreitol and 1 unit of each of both the T4 phage DNA ligase and DNA polymerase enzymes are then added to this mixture. This reaction mixture, with a final volume of 20 µl, is incubated for 60 min at 37° C., and then 5 µl of this are then used to transform competent cells of the *E. coli* K12 strain GT869 (Parsot, C. 1986) (thrB1004 pro thi strA hsdS lacZ ΔM15 [F' lacZ ΔM15 lacIq traD36 proA+ proB+]) according to the method described by Sambrook et al. (1989). The transformed cells are plated out onto Petri dishes containing LB medium supplemented with 100 mg/l of carbenicillin. Twelve clones resistant to the antibiotic are reisolated on the same medium. The single-stranded DNA corresponding to the phagemids of these clones is prepared and sequenced according to the dideoxy method (Sanger et al., 1977). The M13 sequencing kit (Boehringer Mannheim, Mannheim, Germany) and the deoxyadenosine 5'-(α-thio) triphosphate (1300 Ci/mmol, Amersham) are combined according to the suppliers' indications. Four primers are used to determine the sequence of the thyA alleles:

Oligodeoxynucleotide 3 SEQ ID NO: 3): 5'GGTGTGAT-CATGATGGTC

Oligodeoxynucleotide 4 SEQ ID NO: 4): 5'CCTGCAA-GATGGATTCCC

Oligodeoxynucleotide 5 SEQ ID NO: 5): 5'CGCGCCGCAT-TATTGTTTC

Oligodeoxynucleotide 6 SEQ ID NO: 6): 5'GTCTGGACCG-GTGGCGACA

The plasmid pTS1 thus obtained propagates the thyA:Val146 allele, in which position 146 occupied in the wild-type thyA gene by the UGC codon of cysteine is occupied by the GUA codon of valine. The plasmid pTS1 is introduced by transformation, carried out according to the method of Sambrook et al. (1989), into the *E. coli* K12 ΔthyA strain, β1308 (Lemeignan et al., 1993), in which the chromosomal thymidylate synthase gene, thyA, is deleted. The transformed strain carrying the thyA:Val146 plasmid allele, β5366, is shown to be incapable of growing without thymine or thymidine being added to the culture medium, as is the strain β1308 from which it derives. On the other hand, the strain β5366 shows marginal growth at 30° C. on a cysteine diffusion gradient prepared in Petri dishes containing 25 ml of glucose MS mineral medium, starting from a central well containing 0.1 ml of a 400 mM L-cysteine solution. Under the same conditions, the strain β1308 gives rise to no detectable growth. Thus, the missense mutation which converts the catalytic cysteine at position 146 of thymidylate synthase to valine can be partially suppressed by supplying very large amounts of exogenous cysteine. The addition of 0.1 mM of valine to the medium of the Petri dishes abolishes the growth of the strain β5366 on a cysteine gradient. Thus, it is as though the cysteine can infiltrate into the valyl-tRNA synthetase active site to form erroneous Cys-tRNAs$^{Val}$ capable of correcting the substitution of the cysteine in the thymidylate synthase active site, with valine. The excess of valine would prevent the formation of these erroneous Cys-tRNAs$^{Val}$.

Example 2

Construction of an *E. coli* strain including a Cys→Ile missense mutation at the thymidylate synthase active site and creating a nutritional requirement for thymine, thymidine or cysteine.

The corresponding construction is also carried out in order to replace the cysteine at position 146 of thymidylate synthase, by site-directed mutagenesis using oligonucleotide 2, according to the same protocol as in Example 1.

Oligodeoxynucleotide 2 (SEQ ID NO: 2): 5' pTG-GATAAAATGGCGCTGGCACCGATACATG-CATTCTTCCAGTTCTATGT The plasmid pTS2 thus obtained propagates the thyA:Ile146 allele in which position 146 occupied in the wild-type thyA gene by the UGC codon of cysteine is occupied by the AUA codon of isoleucine. The strain which propagates the thyA:Ile146 plasmid allele, β5274, is shown to require the nutritional supply of thymine, of thymidine or of cysteine in excess, as was the strain β5366. The phenotypic suppression of the strain β5274 by the cysteine is abolished with 0.1 mM of isoleucine, as was that of the strain β5366 with valine. Thus, it is as though the isoleucyl-tRNA synthetase is capable of forming erroneous Cys-tRNAs$^{Ile}$ in the presence of an excess of cysteine, and that this erroneous formation is prevented by the presence of an excess of isoleucine.

Example 3

Selection of genetic code mutants which misincorporate cysteine instead of valine, by serial culturing in liquid, and genetic characterization of the valyl-tRNA synthetase mutants thus obtained.

The strain β5366 carrying the thyA:Val146 missense allele on the plasmid pTS1 is cultured in glucose MS mineral medium (2 g/l, Richaud et al., 1993) supplemented with 0.3 mM of thymidine, for 24 h at 30° C. in aerobiosis. The cells are then washed twice with deoxygenated MS mineral medium. A deoxygenated nutrient medium containing 10 ml of glucose MS mineral medium supplemented with 1.5 mM of cysteine is inoculated at 1/100 using the washed cells. The cells are then cultured in anaerobiosis for 24 h at 30° C., and a fresh tube containing 10 ml of deoxygenated cysteine glucose MS mineral medium is inoculated with a 1/100 dilution of the previous culture in the stationary phase. This procedure is repeated 26 times. At the end of this serial propagation, 12 clones from the liquid culture are isolated on plates containing thymidine (0.3 mM) glucose (2 g/l) MS mineral medium, in aerobiosis, and stored in suspension in the same liquid medium at −80° C. The twelve clones are tested on plates containing glucose MS mineral medium supplemented with nutrient factors. All these clones are shown to require thymine or thymidine as a growth factor, unless cysteine is present in the culture medium, at a concentration of at least 1.5 mM.

Two such clones are chosen for a thorough genetic characterization, β8144 and β8146. Experiments involving transduction, using the P1 phage, of the kanamycin resistance characteristic, introduced into the nrdD locus neighboring the valS gene of valyl-tRNA synthetase (97 min of the E. coli K12 chromosome), are carried out using the strains β8144 and β8146. In both cases, approximately half the kanamycin-resistant transductants also show nutrient dependency for thymidine, which can be suppressed with exogenous cysteine at the concentration of at least 1.5 mM. This proportion is in agreement with the genetic distance between the valS and nrdD genes (0.4 min) and implies that the phenotype of suppression of the Cys→Val missense mutation at the thymidylate synthase active site with low concentrations of cysteine is caused by the genetic modification of the valS locus.

The establishment of a genetic modification in the valS gene of the modified strains is confirmed by sequencing this locus: an A changed to a C causes the replacement of the lysine at position 277 with glutamine in the two modified strains β8144 and β8146. The sequencing is performed on a matrix obtained via a polymerase chain reaction (PCR) carried out under conditions described by Sambrook et al. (1989). The amplification reaction is carried out in 100 µl of a solution containing 10 ng of genomic DNA of the strain β8144 or β8146, 20 pmol of each primer, 40 nmol of an equimolar mixture of the 4 deoxynucleotide triphosphates, and 10 µl of a buffer composed of 100 mM Tris-HCl pH 8.3, 500 mM KCl and 20 mM $MgCl_2$, in the presence of 1 to 2 units of Vent polymerase (Biolabs). For each reaction, 30 polymerization cycles are performed, using a DNA amplifier (Perkin-Elmer Cetus), as follows: the denaturation is carried out at 94° C. for 5 min for the 1st cycle and 1 min for the subsequent cycles, the hybridization at 58° C. for 1 min and the elongation at 72° C. for 3 min for the first 29 cycles and for 10 min for the last cycle. Oligonucleotudes 7 and 8 are used for amplifying the gene.

Oligodeoxynucleotide 7 (SEQ ID NO: 7): 5'GGGGAAT-TCGGTGTGTGAAATTGCCGCAGAACG

Oligodeoxynucleotide 8 (SEQ ID NO: 8): 5'GGCAAGCT-TCCAGTATTTCACGGGGAGTTATGC

The PCR fragments thus obtained are purified using the "QIAQUICK" kit (Qiagen) and sent to the company Genaxis in order to determine the sequence thereof.

Example 4

Phenotypic suppression by metabolic precursors of cysteine.

The nutrient requirement for cysteine of the modified strains β8144 and β8146 is exploited in order to characterize metabolic precursors which may substitute for cysteine in the culture medium without giving rise to degradation by oxidation. S-carbamyl-L-cysteine (3 mM), S-methyl-L-cysteine (3 mM) and L-thiazolidine-4-carboxylic acid (2 mM) prove to be capable of replacing cysteine as a growth factor for the modified strains β8144 and β8146, instead of thymidine or thymine. The same compounds prove to be capable of satisfying the cysteine requirement of a cysN::kan mutant (strain JT1, provided by M. Berlyn, Coli Genetic Stock Center, Yale University, USA (Levh et al., 1988)). However, the addition of none of these substances allows growth of the strain β1308 carrying a chromosomal deletion of the thyA gene of thymidylate synthase, thus excluding their contamination with traces of thymine or of thymidine.

Example 5

Selection of genetic code mutants which misincorporate cysteine instead of valine, by isolation on solid medium, and genetic characterization of the valyl-tRNA synthetase mutants which misincorporate cysteine.

The strain β5366 carrying the thyA:Val146 missense allele on the plasmid pTS1 is transduced with a P1 phage lysate harvested on an E. coli auxiliary strain (β7170, Bouzon et al., 1997) into the chromosome of which a kanamycin resistance marker had been introduced at the nrdD locus, neighboring the valS locus of the valyl-tRNA synthetase gene, thus producing the strain β5419. A mutator allele of the dnaQ gene is introduced extemporaneously by transduction of the strain β5419 using a P1 phage lysate harvested on an auxiliary strain (MS2131, Shapiro 1990) carrying a tetracycline resistance marker dnaQ::miniTn10. Such a tetracycline-resistant clone showing a spontaneous mutation rate amplified approximately 1000-fold (for the acquisition of streptomycin resistance) is cultured at 30° C. in glucose minimum medium in the presence of thymidine (0.3 mM). After 24 h, the cells are harvested and washed twice in an identical volume of culture medium without thymidine. A 0.1 ml volume of the resulting suspension, corresponding to approximately $10^8$ bacteria, is plated out on the surface of a series of Petri dishes containing a concentration of S-carbamyl-L-cysteine ranging between 0 and 8 mM by 1 mM increment, adding the glucose (2 g/l) MS mineral medium. The same procedure is applied to the non-mutator strain β5419, to the wild-type dnaQ gene. All the Petri dishes are incubated for 96 h at 30° C. Colonies appear on the dishes having a concentration of S-carbamyl-L-cysteine which exceeds 2 mM, only when the dnaQ::miniTn10 mutator allele has been introduced into the strain tested.

A P1 phage lysate harvested from such a clone is used to transduce the strain β5366 carrying the thyA:Val146 plasmid allele. Approximately half the kanamycin-resistant transductants are shown to be capable of growing in the presence of 3 mM of S-carbamyl-L-cysteine and in the absence of thymine or of thymidine, among which transductants, the strain β5455. The other half of the transductants is incapable of this and requires thymine or thymidine in order to proliferate, as does the strain β5366. This proportion between the phenotypes is in agreement with the genetic distance between the valS and nrdD loci (0.4 min). Thus, the suppression of the Cys→Val thyA missense mutation with a low concentration of exogenous cysteine might result from modification of the valyl-tRNA synthetase gene. The valS locus of one of the strains obtained by transduction of β5366 and capable of growing in the presence of 3 mM of S-carbamyl-L-cysteine and in the absence of thymine or of thymidine, referred to as β5455, is amplified by polymerized chain reaction and sequenced as described in Example 3. An A changed to a C causes the replacement of the threonine at position 222 with proline, thus confirming the establishment of a genetic modification in the valS gene of the strain β5455.

Example 6

Sensitivity of the valyl-tRNA synthetase mutants to non-canonical amino acids.

The strains β5455, β8144 and β8146 are tested for their sensitivity to artificial amino acids which show steric resemblance to valine. The test is carried out on dishes containing glucose of MS mineral medium supplemented with thymidine. The cells are cultured in aerobic medium (glucose MS mineral medium, 0.3 mM thymidine) for 24 h at 30° C. and diluted to 1/250 in MS mineral medium. 0.5 ml of this cell suspension is plated out onto Petri dishes containing 25 ml of glucose MS mineral medium. A well is then hollowed out at the center of the dish and filled with 0.1 ml of an amino acid solution:

(1) 100 mM L-2-aminobutyrate (2) 100 mM L-2-aminovalerate (3) 100 mM L-2,3-diaminopropionate (4) 50 mM L-3-thiol-2-aminobutyrate.

The dishes are then incubated for 24 h at 30° C. and the possible appearance on the dishes of a zone of inhibition around the well is recorded. The diameters of the limited zones of growth inhibition on Petri dishes are measured:

L-2-aminobutyrate: 5.2 cm (β5455), 5.7 cm (β8144), 6.7 cm (β8146);

L-2-aminovalerate: 2.1 cm (β5455), 1.5 cm (β8144), 6.7 cm (β8146);

L-2,3-diaminopropionate: 2.3 cm (β5455), 2.7 cm (β8144), 1.9 cm (β8146);

L-3-thiol-2-aminobutyrate: 2.0 cm (β5366), 4.6 cm (β5455), 4.0 cm (β8144), 4.0 cm (β8146).

L-2-aminobutyrate, L-2-aminovalerate and L-2,3-diaminopropionate, at the concentrations indicated, have no effect on the strain β5366 containing the wild-type valS allele, but inhibit the growth of the strains carrying a mutated valS gene. L-3-thiol-2-aminobutyrate inhibits the growth of all the strains, but a more significant inhibition may be noted on the mutated strains. Thus, it is as though the valyl-tRNA synthetase mutants have a broadened specificity making them capable of charging tRNAs$^{val}$ with amino acids which cannot be incorporated by the wild-type form of the enzyme.

Example 7

Incorporation of the noncanonical amino acid "L-aminobutyrate" into the proteins of an E. coli strain mutated in valyl-tRNA synthetase.

A P1 phage lysate obtained from the strain β5455 (see Example 5), was used to transduce the strain CU505 carrying an ÆilvCABD deletion and a leu mutation making it auxotrophic for valine, isoleucine and leucine. The strain CU505 was obtained from the Coli Genetic Stock Center, at Yale University (USA). Transductant clones were selected on kanamycin LB plates and tested for their sensitivity to aminobutyrate (3 mM) in solid glucose (2 g/l) MS medium containing 0.3 mM of each of the three amino acids valine, isoleucine and leucine. Approximately 50% of the transductant clones could not grow under these conditions, indicating the cotransduction of the valS:T222P allele and the resistance marker nrdD::kan (see Example 5). One of the transductant clones, referred to as β5498, was used to demonstrate the incorporation of aminobutyrate as a replacement for valine, in comparison with CU505. The two strains were cultured at 30° C. in glucose (2 g/l) MS liquid medium containing the Ile-Leu dipeptide at the concentration of 0.3 mM and the Ile-Val dipeptide at the concentration of 0.02 mM, either in the presence of 0.2 mM of L-aminobutyrate or in the absence of the analog. The inoculum corresponding to each strain originated from a preculture in glucose (2 gl) MS liquid medium containing the Ile-Leu dipeptide at the concentration of 0.3 mM and the Ile-Val dipeptide at the concentration of 0.04 mM. The cultures (50 ml) in stationary phase after 24 h at 30° C. were harvested by centrifugation. For each test, the pellet was then resuspended in 25 ml of a solution of trichloroacetic acid at 100 g/l (10% TCA) at 4° C., centrifuged, resuspended in 5 ml of 10% TCA, centrifuged again, the pellet resuspended in 5% TCA, the suspension incubated at 95° C. for 30 min and centrifuged, the pellet resuspended in 5 ml of acetone and centrifuged, the pellet resuspended in 5 ml of acetone and centrifuged, the pellet resuspended in 5 ml of acetone and centrifuged, and the pellet left to dry. The residue thus obtained was dissolved in 1 ml of a solution of $NH_4HCO_3$ at 50 mM in order to be lyophilized. The lyophilizate was dissolved in 2 ml of 6N hydrochloric acid containing 2 g/l of phenol, and the mixture was sealed in a vial and then incubated at 110° C. for 20 h. The amino acid concentration of the hydrolysate was then quantified by derivatization with ninhydrin according to the instructions recommended by the supplier of the Beckman 6300 analyzer. The aminobutyrate was detected in the protein hydrolysate only when the aminobutyrate had been added to the culture medium, and only for the strain β5498. The aminobutyrate proportion replaced a quarter of the amount of valine, corresponding to approximately 5 aminobutyrate residues for 100 amino acids of the total proteins. The detailed results of the analyses for the two strains CU505 and β5498, under the two culture conditions, are given in the table below.

| Chemical composition of the proteins extracted from strains auxotrophic for valine and cultured with valine limiting, with or without aminobutyrate | | | | |
|---|---|---|---|---|
| Amino acid incorporated into the proteins | CU505 wt valS − Abu | β5498 valS T222P − Abu | CU505 wtvalS + Abu | β5498 valS T222P + Abu |
| Abu | 0 | 0 | 0 | 0.20 |
| Val | 0.83 | 0.79 | 0.83 | 0.61 |
| Val + Abu | 0.83 | 0.79 | 0.83 | 0.81 |
| Ala | 1.32 | 1.28 | 1.32 | 1.22 |
| Ile | 0.61 | 0.61 | 0.61 | 0.61 |

Results expressed in Leu equivalents

Example 8

Selection of novel genetic code mutants using a mutator strain, for isolation on solid medium.

The strain β5419, expressing the thyA:Val146 inactive allele on a plasmid and carrying the marker ÆnrdD::kan in the chromosome, as reported in the construction thereof described in Example 5, was transduced using a P1 phage lysate harvested on the strain TAD, carrying a mutator marker ÆmutS::spc, conferring spectinomycin resistance, selecting on LB solid medium containing spectinomycin (25 mg/l) so as to obtain the strain β5555. The mutator phenotype of this strain was demonstrated by counting the frequency of rifamycin-resistant mutants. Following the experimental procedure described in Example 5, clones capable of growing at 30° C. in glucose mineral medium without thymidine, in the presence of 2 to 5 mM of S-carbamoyl-L-cysteine (SCC), were obtained. Three of these clones were used to prepare P1 phage lysates which were used to transduce the strain β5366, selecting for kanamycin resistance, according to the procedure of Example 5. For each of the three lysates, approximately half the transductants were capable of growing in solid glucose mineral medium containing 3 mM of SCC, indicating the proximity of a mutation suppressing the thyA:C146V missense allele and of the marker nrdD::kan. The valS locus of the three strains β5479, β5485 and β5486, each corresponding to an SCC-suppressible transductant obtained from one of the three lysates, was amplified by PCR and sequenced as described in Example 3. A different point mutation was found for each of the three strains, namely Arg 223 changed to His in the strain β5479, Val 276 changed to Ala in the strain β5485 and Asp 230 changed to Asn in the strain β5486. Thus, each clone exhibiting a phenotype of suppression of the Cys 146 Val missense mutant of thyA also exhibits the aminobutyrate sensitivity. Each one of these clones was shown to carry a different point mutation in the valS gene, validating the selective screen as a means of diversifying the activity of valyl-tRNA synthetase in *Escherichia coli*.

BIBLIOGRAPHY

BAIN J. D., E. S. DIALA, C. G. GLABE, D. A. WACKER, M. H. LYTTLE, T. A. DIX and A. R. CHAMBERLIN, 1991; Site-specific incorporation of nonstructural residues during in vitro protein biosynthesis with semisynthetic aminoacyl-tRNAs, Biochemistry 30: 5411-5421.

BOUZON, M. and P. MARLIERE, 1997; Human deoxycytidine kinase as a conditional mutator in *Escherichia coli*. C.R. Acad. Sci. Paris 320: 427-434.

KUNKEL, T. A., and J. D. ROBERTS, 1987; Rapid and efficient site-specific mutagenesis without phenotypic selection. Methods Enzymol. 154: 367-382.

LEMEIGNAN, B., P. SONIGO and P. MARLIERE, 1993; Phenotypic suppression by incorporation of an alien amino acid. J. Mol. Biol. 231: 161-166.

LEVH, T. F., J. C. TAYLOR and G. D. MARKHAM, 1988; the sulfate activation locus of *Escherichia coli* K12: cloning, genetic, and enzymatic characterisation. J. Biol. Chem. 263: 2409-2416.

PARSOT, C., 1986; Evolution of biosynthetic pathways: a common ancestor for threonine synthase, threonine dehydratase and D-serine dehydratase. EMBO J., 5: 3013-3019.

RICHAUD, C., D. MENGIN-LECREULX, S. POCHET, E. J. JOHNSON, G. N. COHEN et al., 1993; Directed Evolution of Biosynthetic pathways. J. Biol. Chem. 268: 26827-26835.

SAMBROOK, J., E. F. FRITSCH and T. MANIATIS, 1989; Molecular cloning: A Laboratory Manual. Cold Spring Harbor Laboratory Press, Cold Spring Harbor, N.Y.

SANGER, F., S. NICKLEN and A. R. COULSON, 1977; DNA sequencing with chain-terminating inhibitors. Proc. Natl. Acad. Sci. USA. 74: 5463-5467.

SHAPIRO, J. A. 1990; Action of a transposable element in coding sequence fusions. Genetics 126: 293-299.

The invention claimed is:

1. A method for providing bacterial or yeast cells with the capacity to produce a protein, the amino acid sequence of which comprises at least one unconventional amino acid, comprising:

(a) introducing at least one missense mutation in a target codon of a gene encoding a protein required for the growth of the bacterial or yeast cells, wherein the mutated protein synthesized from the mutated gene is not functional in the bacterial or yeast cells; and (b) selecting the bacterial or yeast cells obtained in (a) in a culture medium which (1) does not contain a nutrient compensating for the loss of functionality of the mutated protein and (2) contains an unconventional amino acid which restores the functionality of said protein required for growth of the bacterial or yeast cells, said unconventional amino acid being that encoded by said target codon; and (c) culturing the bacterial or yeast cells obtained in (b) in a culture medium containing said amino acid encoded by said target codon.

2. The method of claim 1, further comprising an additional culturing in a culture medium containing a nutrient compensating for the loss of functionality of the mutated protein.

3. The method according to claim 1, wherein the step of culturing the cells comprises a series of cultivation steps of the same cells under selective conditions until mutants capable of growing in the absence of the nutrient required by loss of the functionality of the mutated protein are obtained.

4. The method of claim 1, wherein the missense mutation is chosen from missense mutations which spontaneously reverse at a frequency of one organism from at least $10^{15}$.

5. The method of claim 1, wherein the missense mutation transforms a target codon of a gene encoding a protein required for the growth of said cell into a codon, which, in comparison with the target codon, exhibits a change of at least two bases.

6. The method of claim 1, wherein the target codon encodes an amphiphilic amino acid.

7. The method of claim 1, wherein the target codon encodes an amino acid which has a steric volume which is the same as or smaller than the steric volume of the amino acid encoded by the missense mutation.

8. The method of claim 5, wherein the target codon encodes cysteine.

9. The method of claim 5, wherein the amino acid encoded by the missense mutation is valine or isoleucine.

10. The method of claim 1, wherein said introducing is carried out using a vector comprising the mutated sequence of said gene encoding a protein required for the growth of said cells, including said missense mutation.

11. The method of claim 10, wherein said vector is a plasmid vector.

12. The method of claim 1, further comprising isolating the cells which grow in said culturing of c).

13. The method of claim 12, further comprising culturing the isolated cells in a second culture medium containing said amino acid encoded by said target codon.

14. The method of claim 13, wherein the concentration of said amino acid in said second culture medium is at a concentration higher than the concentration of said amino acid in said first culture medium, and wherein the method further comprises selecting the cells sensitive to the concentration of said amino acid in said second culture medium.

15. The method of claim 12, wherein an aminoacyl-tRNA synthetase which recognizes the amino acid encoded by said missense mutation of said selected cells is capable of charging onto one of its associated tRNAs an unconventional amino acid or an amino acid other than said amino acid encoded by said missense mutation.

16. The method of claim 15, wherein the nucleic acid sequence of the gene encoding said aminoacyl-tRNA synthetase includes at least one mutation compared with the sequence of the corresponding wild-type gene.

17. The method of claim 16, wherein said mutation in the nucleic acid sequence of the gene encoding said aminoacyl-tRNA synthetase is generated in vivo.

18. A process for producing a protein the amino acid sequence of which comprises said at least one unconventional amino acid, comprising:

(a) selecting a cell by the method according to claim 12;

(b) growing said cell selected in (a) in a culture medium comprising said unconventional amino acid or a precursor thereof and under culture conditions which allow the growth of said cell, and (c) producing a supernatant or a cell pellet from the cell culture; and (d) isolating from the culture supernatant and/or from the cell pellet produced in step (c) a protein comprising said unconventional amino acid.

19. The process of claim 18, wherein cell culture medium in (b), which allows the growth of said cell, contains a precursor of said unconventional amino acid.

20. The process of claim 18, wherein said unconventional amino acid is synthesized by said cell.

21. The process of claim 20, wherein the synthesis of said unconventional amino acid is increased by genetic modification of said cell.

22. The process of claim 18, wherein said cell is auxotrophic for the amino acid encoded by said target codon.

23. The process of claim 18, wherein said cell comprises a homologous or heterologous gene of interest the coding sequence of which includes at least one target codon.

24. The process of claim 23, wherein the culture medium for growing cells in (b) further comprises the compounds required for inducing the synthesis of the protein encoded by said gene of interest.

25. The process of claim 23, wherein the biological activity of the protein encoded by said gene of interest is at least partially conserved after the incorporation of said unconventional amino acid at the level of the target codon of said gene of interest.

26. An *E. coli* cell, obtainable by the method of claim 1, wherein said cell comprises valyl-tRNA synthase including one mutation selected from the group consisting of K277Q, R223H, V276A and D230N, which allows said valyl-tRNA synthase to charge compounds that show steric resemblance to valine.

27. The isolated cell of claim 26, which is selected from the group consisting of the following cells deposited at the CNCM (Collection Nationale de Culture de Microorganismes, Paris, France):

(a) *E. coli* strain deposited at the CNCM under the No. I-2026 on May 25, 1998, (b) *E. coli* strain deposited at the CNCM under the No. I-2027 on May 25, 1998, (c) *E. coli* strain deposited at the CNCM under the No. I-2339 on Oct. 26, 1999, (d) *E. coli* strain deposited at the CNCM under the No. I-2340 on Oct. 26, 1999, and (e) *E. coli* strain deposited at the CNCM under the No. I-2341 on Oct. 26, 1999.

28. The *E. coli* cell of claim 26, wherein said cell comprises valyl-tRNA synthase including a mutation of K277Q.

29. The *E. coli* cell of claim 26, wherein said cell comprises valyl-tRNA synthase including a mutation of R223H.

30. The *E. coli* cell of claim 26, wherein said cell comprises valyl-tRNA synthase including a mutation of V276A.

31. The *E. coli* cell of claim 26, wherein said cell comprises valyl-tRNA synthase including a mutation of D230N.

32. The *E. coli* cell of claim 26, wherein the compounds that show steric resemblance to valine are selected from the group consisting of cysteine, L-2-aminobutyrate, L-2-aminovalerate, L-2,3-diaminopropionate and L-3-thiol-2-aminobutyrate.

33. A method of producing a protein the amino acid sequence of which comprises said unconventional amino acid, comprising culturing the isolated cell of claim 26 under conditions to produce the protein.

34. An *E. coli* cell, which comprises valyl-tRNA synthase including at least one mutation of K277Q, R223H, V276A or D230N, which allows said valyl-tRNA synthase to charge compounds that show steric resemblance to valine.

35. The *E. coli* cell of claim 34, wherein said cell comprises valyl-tRNA synthase including a mutation of K277Q.

36. The *E. coli* cell of claim 34, wherein said cell comprises valyl-tRNA synthase including a mutation of R223H.

37. The *E. coli* cell of claim 34, wherein said cell comprises valyl-tRNA synthase including a mutation of V276A.

38. The *E. coli* cell of claim 34, wherein said cell comprises valyl-tRNA synthase including a mutation of D230N.

39. The *E. coli* cell of claim 34, wherein the compounds that show steric resemblance to valine are selected from the group consisting of cysteine, L-2-aminobutyrate, L-2-aminovalerate, L-2,3-diaminopropionate and L-3-thiol-2-aminobutyrate.

40. The *E. coli* cell of claim 26, wherein said compounds that show steric resemblance to valine is cysteine.

41. The *E. coli* cell of claim 34, wherein said compounds that show steric resemblance to valine is cysteine.

42. A process for producing a protein the amino acid sequence of which comprises at least one unconventional amino acid, comprising:
 (a) growing the cell of claim 34 in a culture medium comprising at least one unconventional amino acid and under culture conditions which allow the growth of said cell, wherein said unconventional amino acid is selected from the group consisting of cysteine, L-2-aminobutyrate, L-2-aminovalerate, L-2,3-diaminopropionate and L-3-thiol-2-aminobutyrate,
 (b) producing a supernatant or a cell pellet from the cell culture; and
 (c) isolating from the culture supernatant and/or from the cell pellet produced in step (b) a protein comprising said unconventional amino acid.

* * * * *